United States Patent [19]

Hamada et al.

[11] Patent Number: 4,628,573

[45] Date of Patent: Dec. 16, 1986

[54] PROCESS FOR PRODUCING ARRAY-TYPE ULTRASONIC PROBE

[75] Inventors: Akira Hamada; Keiichi Ohira; Akira Funakoshi, all of Iwaki, Japan

[73] Assignee: Kureha Kagaku Kogyo Kabushiki Kaisha, Tokyo, Japan

[21] Appl. No.: 657,489

[22] Filed: Oct. 4, 1984

[30] Foreign Application Priority Data

Oct. 5, 1983 [JP] Japan .................................. 58-185178

[51] Int. Cl.⁴ .............................................. H04R 17/00
[52] U.S. Cl. ........................................ 29/25.35; 29/418
[58] Field of Search ................ 29/25.35, 418; 310/334, 310/335, 367, 368, 369

[56] References Cited

U.S. PATENT DOCUMENTS 2,956,184 10/1960 Pollack ................................. 29/25.35
3,059,130 10/1962 Robins .................................. 29/25.35
4,401,910 8/1983 Beerman ............................... 310/334

FOREIGN PATENT DOCUMENTS 843827 8/1960 United Kingdom ............... 29/25.35

Primary Examiner—Howard N. Goldberg
Assistant Examiner—P. W. Echols
Attorney, Agent, or Firm—Wenderoth, Lind & Ponack

[57] ABSTRACT

Array type ultrasonic probes including those of the annular array type and the linear array type are produced with a high accuracy of arrangement of unit transducer elements by first providing an integral processed plate wherein unit back electrodes are almost configurated into their final shapes but connected with each other by connecting portions so as to facilitate the handling thereof as an integral plate. The integral processed plate is bonded to a substrate and the connecting portions are removed to leave the back electrodes separately bonded to the substrate. On the back electrodes, a piezoelectric polymer film and a front electrode are applied to give an array type ultrasonic probe adapted for medical diagnosis.

10 Claims, 11 Drawing Figures

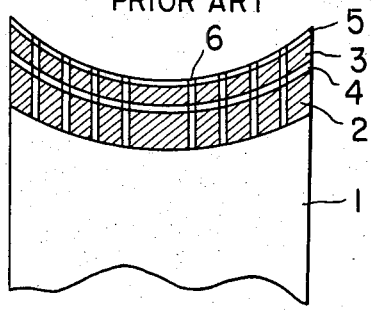
FIG. 1(a)
PRIOR ART
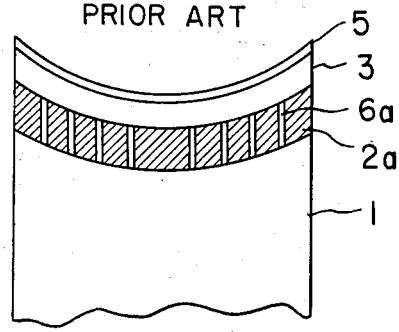
FIG. 2(a)
PRIOR ART
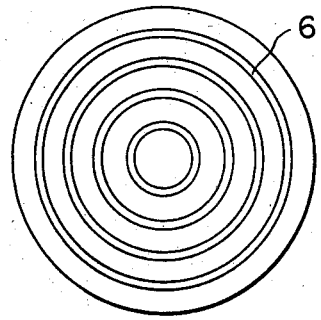
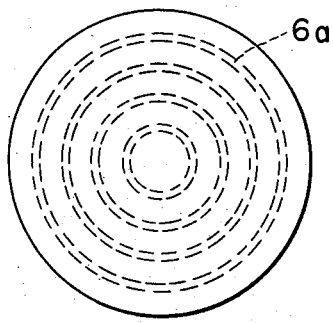
FIG. 1(b)
PRIOR ART
FIG. 2(b)
PRIOR ART
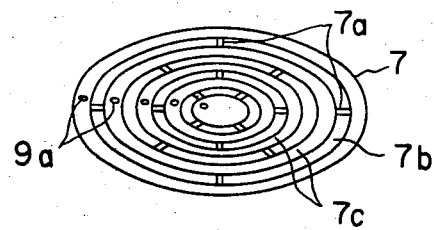
FIG. 3(a)
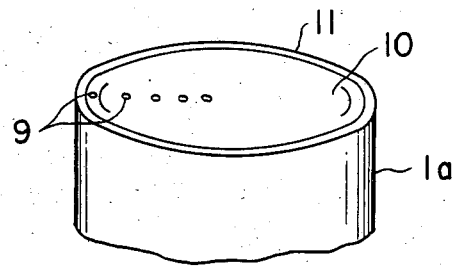
FIG. 3(b)

PROCESS FOR PRODUCING ARRAY-TYPE ULTRASONIC PROBE

BACKGROUND OF THE INVENTION

This invention relates to a process for producing an array-type ultrasonic probe using a polymeric piezoelectric film as an ultrasonic transducer element.

Ultrasonic transceivers (transmitter-receivers) have heretofore been widely used, for example, in depth sounders, fish sounders, and ultrasonic detectors. Recently, the application of ultrasonic transceivers to medical diagnostic equipment has been rapidly progressing. The ultrasonic transceiver for medical diagnosis is operated on the principle that an ultrasonic wave generated by the ultrasonic probe is reflected at boundaries between portions of a living body having different acoustic impedances (velocity of sound × density), and the resultant ultrasonic echo received by the ultrasonic probe is subjected to signal-conditioning and displayed on a cathode-ray tube. In the ultrasonic wave generating part of such an ultrasonic probe, a vibrating member comprising a piezoelectric element is used. In order to improve the resolution of sectional plane images in a deep portion of a living body, a higher frequency of ultrasonic wave is gradually required. For complying with this trend, an array-type probe is preferred, wherein the piezoelectric element is divided into a number of small and thin unit elements. The array-type probes are generally classified, according to the arrangement of unit piezoelectric elements, into those of the annular-type wherein fine unit elements having shapes of annular rings with gradually different diameters are radially arranged with a small gap therebetween, and those of the linear-type wherein linear or thin bar-shaped unit elements are arranged in parallel with each other with a small gap therebetween.

Among these, as annular-type probes, for example, those having detailed structures as shown in FIGS. 1(a) and 1(b) or FIGS. 2(a) and 2(b) have heretofore been used wherein FIGS. 1(a) and 2(a) represent partial sectional elevations and FIGS. 1(b) and 2(b) plan views.

A conventional process for producing an annular probe as shown in FIGS. 1(a) and 1(b) will now be explained along with its structure. On a concave upper face of a substrate 1 made of plastics, etc., a metal reflection plate 2 and a ceramic piezoelectric plate 3 having a back electrode 4 and a front electrode 5, each having a curvature corresponding to the concave upper face, are successively disposed by bonding. Thereafter, annular ring-shaped grooves 6 are formed by cutting the laminate by means of a diamond cutter, wire saw, laser beam or abrasive member to leave separate transducer elements each bonded to the substrate 1. Herein, the resultant annular ring-shaped elements are caused to have substantially the same surface areas by gradually changing the widths thereof from the central one to the peripheral one so that the respective ring elements will emit substantially the same energy of ultrasonic waves, while they are drawn to have apparently similar widths in FIGS. 1 through 5 for convenience of drawings.

On the other hand, the structure shown in FIGS. 2(a) and 2(b) is formed by bonding a metal reflection plate 2a onto a substrate 1, forming annular ring-shaped grooves 6a by cutting only the reflection plate 2a, and forming thereon a ceramic piezoelectric plate 3 having only a front electrode 5.

However, the above explained conventional production processes, because of minute processing by cutting involved therein, accompany several disadvantages as follows. Thus, they are time-consuming. Cooling water, cooling oil or other coolants give ill effects to both post-processing and product characteristics. The cutting operation sometimes results in separation between the substrate and the reflection plate or between the reflection plate and the piezoelectric member, complete or partial separation, breakage or fracture of the reflection plate or the piezoelectric plate, and poor insulation at separating grooves or lowering or limitation in accuracy of working of separating grooves due to incomplete removal of cutting residues. Further, when a polymer dielectric film is used in place of the ceramic dielectric plate in the above mentioned conventional processes in order to comply with the requirement of a thin piezoelectric member, the piezoelectric performance of the polymer piezoelectric film is deteriorated due to cutting heat from cutting. These circumstances are not peculiar to the production of annular array-type probes but hold true with the production of the array-type ultrasonic probes in general including those of linear arrangement, wherein small unit piezoelectric elements are arranged with small gaps or intervals on a substrate.

In order to remove the difficulties as mentioned above accompanying the cutting of a reflection plate bonded onto a substrate, it may be conceivable to produce a structure shown in FIGS. 2(a) and 2(b) by producing individual units of back electrode and reflection plate 2a in advance by cutting and the like processing, and bonding them one by one onto the upper face of the substrate 1. One difficulty with this approach is that the structure of FIG. 2, when compared with that of FIG. 1, tends to give a lower element division or separation performance by separating grooves 6a and result in poor performances because of the use of a uniformly extending front surface electrode, especially in the case where the piezoelectric member 3 is thick, as is the case with a ceramic piezoelectric member. Moreover, in the case of an array-type ultrasonic probe for use in a medical diagnostic instrument, an extremely accurate arrangement is required such that reflection plates having a 1 mm-width, for example, are arranged with a uniform gap of 0.05 mm therebetween, and it is almost impossible to perform such an accurate arrangement by successive bonding of unit reflection plates. This is particularly true when the upper surface of a substrate 1 to which the reflection plates are applied are made concave in order to enhance the ultrasonic transmitting and receiving performance.

As another approach, a structure of FIG. 2 may be formed by bonding a uniform layer of reflection plate 2a onto a substrate 1 and thereafter etching the reflection plate 2a to form separating grooves 6a therein. In this case, however, are accompanied several problems such as deterioration of the adhesive by the etchant, complete or partial separation of the reflection plate, and lowering in accuracy of working of separating grooves due to over-etching, undercutting, etc.

SUMMARY OF THE INVENTION

A principal object of the present invention is, by resolving the problems mentioned above of the conventional or other related processes, to provide a process for readily providing an array-type ultrasonic probe wherein individual unit piezoelectric elements are accurately arranged.

As the result of our studies with the above object, in producing an ultrasonic probe substantially as shown in FIG. 2, we have found it effective to prepare in advance an integral processed plate from a blank conductor plate wherein unit back electrode and reflection plates are almost configurated into their final shapes but connected with each other to such an extent that the plate can be handled as an integral plate, applying the integral processed plate onto a face of a substrate and removing only the connecting or bridge portions on the substrate, whereby a whole process for production of a probe is remarkably simplified and an accurately separated piezoelectric arrangement structure is obtained.

The process for producing ultrasonic probes according to the present invention is based on the above knowledge.

More specifically, the improved process according to the present invention resides in a process for producing an array-type ultrasonic probe comprising a substrate and a plurality of transducer elements disposed on the substrate, said plurality of transducer elements comprising, in respective order from the substrate surface, a plurality of back electrodes which also serve as reflection plates, a piezoelectric polymer film, and a front electrode disposed in the order named on the substrate which process comprises the steps of:

providing an integral processed plate of a structure comprising said plurality of back electrodes and connecting portions connecting the back electrodes with each other, bonding the integral processed plate onto a receiving face of the substrate, removing the connecting portions to leave the plurality of back electrodes separately bonded to the substrate, and disposing the piezoelectric polymer film and the front electrode on the plurality of back electrodes.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 1(a) and 2(a) respectively represent a partial sectional elevation of a conventional embodiment of an annular array-type ultrasonic probe.

FIGS. 1(b) and 2(b) illustrate corresponding plan views of the above embodiments.

FIGS. 3 to 6 illustrate intermediate steps of an embodiment of the process according to the invention for producing an annular array-type probe, wherein FIGS. 3(a) and 3(b) are partial perspective views of an integral processed plate (reflection plate and back electrode plate) and a substrate, respectively, FIG. 4 is a partial sectional elevation of a combination of an integral processed plate and a substrate also including lead wires, FIG. 5 is a plan view of the combination shown in FIG. 4, FIG. 6 is a sectional view of a polymeric piezoelectric film having thereon only an electrode.

DETAILED DESCRIPTION OF THE INVENTION

Figure 4:
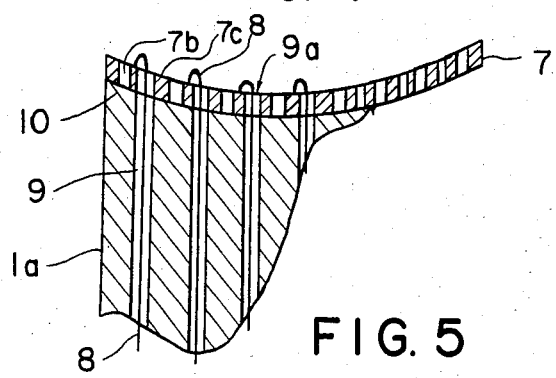

When an annular array type ultrasonic probe is produced according to the invention, there is provided a back electrode plate which also serves as a reflection plate (integral processed plate) 7 having a structure almost similar to that in an ultrasonic probe as the final product but maintaining its integrity by means of bridge portions 7a. Such a back electrode plate 7 may be produced by removing portions corresponding to grooves 7b from a blank circular plate, having a thickness of 0.1 mm and an outer diameter of 25 mm and made of an electrode material such as copper or aluminum, by machining, electric spark processing, laser processing, etching, etc. In this case, whatever method of cutting or processing is applied, substantial problems accompanying a similar cutting or processing of a uniform electrode plate which has already been bonded to a substrate are obviated, and the back electrode plate can be formed easily with a high accuracy. Among the cutting or processing methods available for this purpose, such methods as laser processing, electric spark processing and etching are preferred because they can process a thin electrode plate with less undesirable deformation. Particularly when the etching is adopted, in place of one-face etching required for processing of the electrode plate on a substrate, both-face etching is available, and an etchant, whether it is liquid or gaseous, can be readily refreshed by flowing at portions under processing, whereby accurate processing can be performed without problems such as undercutting.

In one example, the thus formed bridge portions 7a have a length (i.e., width of groove 7b) of 0.1 mm and a width of 0.1 mm, and four bridge portions are provided between an adjacent pair of annular rings 7c. The annular rings have a width of 1.3 mm, 1.4 mm, 1.7 mm and 2.2 mm, respectively, from the periphery toward the inside.

Then, the thus obtained integral processed plate 7 is pressed so as to be given a curvature fitting the curvature of a face for setting element 10 of a substrate 1a (FIG. 3(b)). Such a curvature may also be given to the blank electrode plate before the cutting or processing for making grooves 7b. To each of the individual back electrodes of the thus curved integral processed plate 7, lead wires 8 are connected through bores or passages 9 formed in the substrate 1a, and then the integral processed plate 7 is bonded to the element setting or receiving face 10 of the substrate 1a (FIG. 4). In this case, it is preferred to form a peripheral ridge 11 along the periphery of the element setting face 10 which has a height substantially equal to the thickness of the processed plate 7 and an inner diameter or size closely fitting the periphery of the processed plate 7 because the integral processed plate is thereby readily placed and bonded in the right position of the element setting face 10 (FIG. 3(b)).

In a preferred embodiment of attaching lead wires 8 to the back electrodes, before or after the curving treatment of the integral processed plate 7, the individual back electrodes 7c constituting the processed plate 7 are bored to form bores or perforations 9a. On the other hand, bores or passages 9 are formed in substrate 1a so as to communicate with the bores 9a. Each of the lead wires 8 is threaded through bores 9 and 9a and connected to one of the individual back electrode 7c as shown in FIG. 4.

Figure 5:
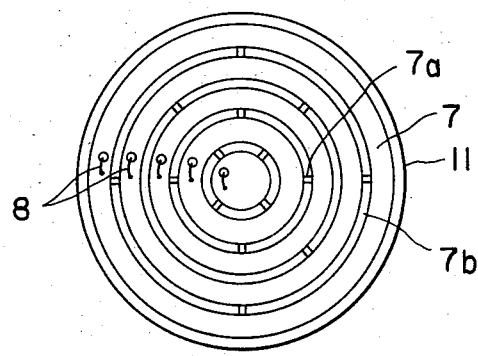
Figure 6:

A plan view of the thus bonded structure is shown in FIG. 5. Bridge portions 7a are then removed, for example, by simple machining or laser processing and thereon a polymeric piezoelectric film 3 of, e.g., 40 microns in thickness having only a front electrode 5 such as of Al or Cu film of, e.g., 0.05 micron in thickness is applied thereon by means of an adhesive, whereby an annular array-type ultrasonic probe having a structure as shown in FIGS. 2(a) and 2(b) is obtained according to the present invention.

The adhesive layer between the back electrode and the piezoelectric film is preferably thin, e.g., 4 microns, because the thinner the layer is, the less the ultrasonic attenuation becomes. Therefore, as the adhesive, a low-viscosity adhesive such as, for example, epoxy type, nitrile-type or acrylate-type adhesive is preferred when used in combination with a piezoelectric film of, for example, a vinylidene fluoride resin including polyvinylidene fluoride.

Figure 7:
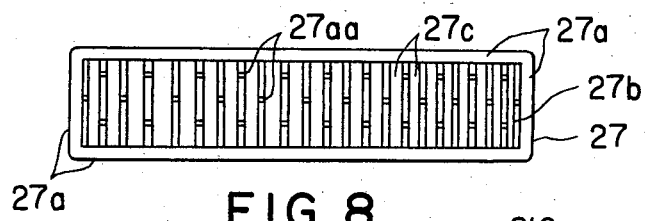
FIGS. 7 and 8 are a plan view of an integral processed plate and a partial perspective view of a substrate, respectively, for illustrating the production of a linear array-type probe.
Figure 8:
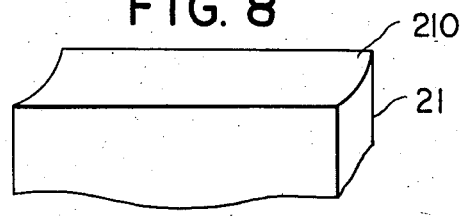

Hereinabove, the present invention has been explained with reference to the production of an annular array-type ultrasonic probe. The process according to the present invention is, however, also applicable to the production of linear array-type ultrasonic probes. In this case, an integral processed plate 27 is provided, having a structure substantially the same as that of a back electrode except for connecting portions 27a and 27aa as shown in a plan view of FIG. 7, which has been obtained by removing portions corresponding to separation grooves 27b from a blank conductor plate. The integral processed plate 27 is applied to an element receiving face 210 of a substrate 21 having a structure as shown in a partial perspective view of FIG. 8. The unnecessary connecting portions 27a or 27aa are removed, for example, by laser processing and machining, followed by connection of lead wires and application of a polymeric piezoelectric film.

In one example, the integral processed plate 27 had a thickness of 0.12 mm and 72 back electrodes 27c of 25 mm in length and 1 mm in width which are spaced apart from each other with a gap of 0.1 mm, connected by bridge portions 27aa having a width of 0.1 mm and surrounded by a peripheral connection member 27a having a width of 5 mm.

In the above examples, the shapes of the ultrasonic transmitting and receiving planes, thus the shapes of element receiving faces of substrate (1, 21), are all concave. It will however be readily understood that the essential advantages of the present invention are similarly obtained regardless of the shape of the ultrasonic transmitting and receiving plane, i.e., whether it is flat, concave or convex.

According to the process of the invention, as described hereinabove, fine accurate separation and arrangement of individual or unit piezoelectric elements, especially those of individual back electrodes, which have been an obstacle to manufacture and performance of array-type ultrasonic probes, can be easily performed. Further, machining steps can be completely eliminated by the use of etching, laser processing or their combination, whereby an accurate arrangement of unit ultrasonic transducer elements can be obtained with little processing or machining defects. Thus, there is obtained an ultrasonic probe having excellent performances both initially and under successive use.

What is claimed is:

1. A process for producing an array-type ultrasonic probe comprising a substrate and a plurality of transducer elements disposed on the substrate, said plurality of transducer elements comprising, in respective order from the substrate surface, a plurality of spaced back electrodes which also serve as reflection plates, a piezoelectric polymer film, and a front electrode, which process comprises the steps of:
   providing an integral processed plate of a structure comprising said plurality of spaced back electrodes and at least one connecting portion which fills less than the entire space between and connects adjacent said spaced back electrodes,
   bonding the integral processed plate onto a receiving face of the substrate,
   removing the at least one connecting portion to leave the plurality of spaced back electrodes separately bonded to the substrate, and
   disposing the piezoelectric polymer film and the front electrode on the plurality of spaced back electrodes.

2. The process for producing an array-type ultrasonic probe according to claim 1, wherein said integral processed plate has been obtained through machining, laser processing, electric spark processing or etching from a blank conductor plate.

3. The process for producing an array-type ultrasonic probe according to claim 1, wherein said integral processed plate has been obtained through etching from a blank conductor plate.

4. The process for producing an array-type ultrasonic probe according to claim 1, wherein the receiving face of the substrate is concave.

5. The process for producing an array-type ultrasonic probe according to claim 1, wherein the receiving face of the substrate has a peripheral ridge having a height substantially equal to the thickness of the integral processed plate and having an inner size closely fitting the periphery of the integral processed plate.

6. The process for producing an array-type ultrasonic probe according to claim 1, wherein a lead wire is connected to each of the back electrodes through a bore formed in the substrate before the step of bonding the integral processed plate onto the substrate.

7. The process for producing an array-type ultrasonic probe according to claim 1, wherein the ultrasonic probe is of an annular array-type and comprises a plurality of spaced annular ring-shaped back electrodes having gradually different diameters and radially arranged with small gaps therebetween on the substrate.

8. The process for producing an array-type ultrasonic probe according to claim 1, wherein the ultrasonic probe is of a linear array-type and comprises a plurality of spaced bar-shaped back electrodes arranged in parallel with each other with small gaps therebetween on the substrate.

9. The process for producing an array-type ultrasonic probe according to claim 8, wherein a peripheral member surrounds and connects the plurality of spaced back electrodes and the at least one connecting portion each comprises an internal bridge member connecting an adjacent pair of the spaced back electrodes.

10. The process for producing an array-type ultrasonic probe according to claim 1, wherein the piezoelectric film comprises a film of a vinylidene fluoride resin.

* * * * *